United States Patent [19]
Ackley

[11] 4,022,203
[45] May 10, 1977

[54] TREATED PATCH FOR MINOR CUTS

[76] Inventor: Win Ackley, 15240 Highland Place, Minnetonka, Minn. 55343

[22] Filed: Jan. 22, 1976

[21] Appl. No.: 651,605

[52] U.S. Cl. .................................. 128/156; 128/325
[51] Int. Cl.² ......................................... A61L 15/00
[58] Field of Search .......... 128/156, 155, 169, 170, 128/325, 296; 206/440

[56] References Cited

UNITED STATES PATENTS

| 1,899,625 | 2/1933 | Metts | 206/440 |
| 2,280,506 | 4/1942 | Betts | 128/156 |
| 2,367,417 | 1/1945 | Milem | 206/440 |
| 2,473,062 | 6/1949 | Kennedy et al. | 128/156 |
| 3,122,479 | 2/1964 | Smith | 128/156 X |
| 3,249,109 | 5/1966 | Maeth et al. | 128/156 X |
| 3,328,259 | 6/1967 | Anderson | 128/156 X |
| 3,491,753 | 1/1970 | Milton et al. | 128/156 |

FOREIGN PATENTS OR APPLICATIONS

| 629,419 | 9/1949 | United Kingdom | 128/325 |
| 1,329,693 | 9/1973 | United Kingdom | 128/325 |
| 522,886 | 6/1940 | United Kingdom | 128/325 |

Primary Examiner—John D. Yasko

[57] ABSTRACT

A patch that is especially adapted to be applied over a minor cut or scratch to aid in stopping the bleeding therefrom. The patch includes a quantity of material effective to reduce bleeding.

7 Claims, 3 Drawing Figures

TREATED PATCH FOR MINOR CUTS

BACKGROUND OF THE INVENTION

This invention relates to patches carrying a medicament or the like that are adapted to be placed over a cut or scratched area of the skin. More particularly to a patch that includes a quantity of material adapted to reduce blood flow such that the user may employ the same when shaving, for instance.

The problems associated with shaving, for example, are well known, cuts, nicks, scratches, etc. and the bleeding associated therewith. Most people either apply a styptic stick thereto followed by a piece of covering material such as tissue, gauze, etc. or follow only one of the foregoing routes. None of the foregoing avenues is completely acceptable, however, due to either the multiple steps involved or the inadequate nature of just the first step.

The prior art teaches a variety of surgical patches and the like, for example, as disclosed in U.S. Pat. Nos. 1,434,779; 1,845,630; 1,861,530; 2,001,862; 2,018,517; 2,068,703; 3,143,208; 3,212,495; 3,741,210; 3,814,095; and others. None of the foregoing, however, provide a means for substantially reducing the flow of blood from a cut with the aid of a substance carried, impregnated or coated onto a substrate to be applied to the area.

SUMMARY OF THE INVENTION

It is accordingly an object of the instant invention to provide for a new and novel means of aiding in the reduction of blood flow from a cut by covering the same with a patch as hereinafter described.

It is another object to provide for a self adhering patch.

It is a further object to provide for the same at relatively little cost thereby making it generally available.

These and other objects and advantages of the invention will become more apparent from the following detailed disclosure and claims and by reference to the accompanying drawings, in which:

Figure 1:
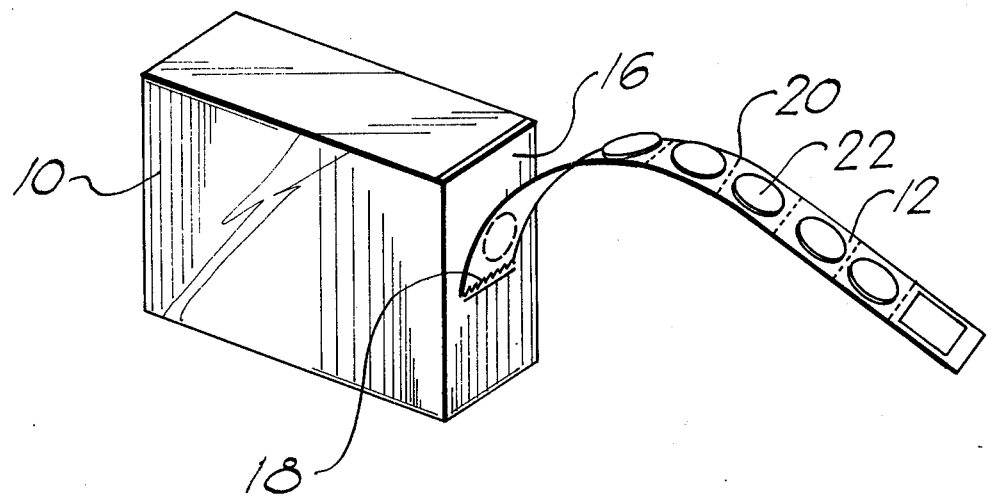
FIG. 1 is a perspective view of an embodiment of the invention in a dispenser.
Figure 2:
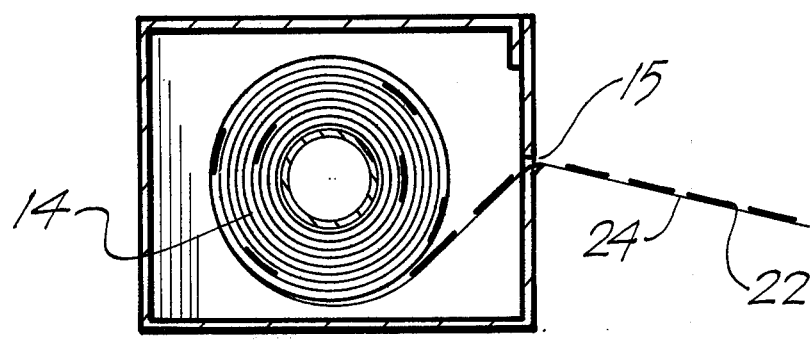
FIG. 2 is a sectional view thereof.
Figure 3:
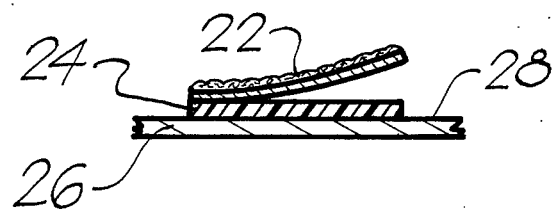
FIG. 3 is a side elevational view of the patch.

Broadly speaking, the instant invention includes the provision of an article for covering a cut area in the skin, comprising a substantially centrally disposed layer of liquid absorbable pad means containing at least a sufficient quantity of a blood coagulating substance, the pad means disposed on a first backing layer having a dimension at least as large as the pad means and being liquid impermeable.

DETAILED DISCLOSURE

Referring more particularly to the drawings there is shown a cartridge 10 that may be employed for dispensing the patch 12 from a roll 14 therein. The orifice 15 in the wall 16 of the dispenser 10 may be serrated 18 to facilitate separation of one patch 12 from the next succeeding one. Each patch 12 may also be separated from the next one by a perforate edge 20 disposed therebetween to facilitate separation. The particular physical form of the patch 12 is not critical to the nature of the invention, nor is the package in which the same is placed.

The patch 12 itself will preferably include a central area 22 that is either coated or impregnated with a sufficient quantity of a blood reducing or skin drying substance, such as aluminum sulfate or the like, which may if desired be combined with a quantity of antibacterial agent, medicament, the like and compatible combinations thereof. The essential active ingredient, generally comprises about 90% of the weight of the impregnate or coating. The impregnate will generally be in dried form for ease of application. Aluminum sulfate is the preferred material.

The commercial product is also known as Cake Alum or Patent Alum. $Al_2(SO_4)_3 \cdot 18H_2O$; mol. wt. 666.40.

It is an Anhydr. salt, having the following composition: 51.34%; $H_2O$, 48.66%; Al, 8.09%: $Al_2O_3$, 15.30%; $SO_3$, 36.04%; $SO_4$, 43.24%. It is about 99.5% pure. The article of commerce usually contains 5–10% less water than the theory.

It is white, lustrous crystals, pieces, granules, or powder. Sp.Gr. 1.61. Melts when gradually heated. At 250° loses its water; decomposes at red heat. Soluble in 1 water; insoluble in alcohol.

On long boiling of the aq. soln., insoluble basic salt ppts. The aq. soln. is acid.

The material is believed to have astringent, antiseptic and caustic properties. The exact mechanism of the operation of reducing blood flow is not fully understood by applicant, though it is believed that its astringent imparting properties do play an essential role.

The core 22 may be any suitable liquid absorbent, non-toxic, nonallergenic, preferably sterile substance that may be derived from woven or non-woven materials that are adapted to form a pad means. The shape thereof is not important. The pad means or core 22 will be disposed on a backing strip 24 that has a dimension at least as large as that of the pad means 22, thereby providing for a barrier between the pad means 22 and the exterior of the patch 12, when the same is in place on the skin. The backing strip 24 will preferably be a liquid impervious layer that may be constructed of any suitable material, e.g., plastic layer and the like.

In another embodiment of the invention, the patch 12 may be disposed on second backing sheet 26 that includes a layer of pressure sensitive adhesive thereon to facilitate engagement of the patch 12 about the treated area of the skin. The dimension of the backing layer 26 being larger than that of the patch 12 thereby providing a perimeter 28 therearound that contains an exposed area 28 of adhesive. Alternatively, the first backing layer 24 may be larger than the core 22 and it may contain the adhesive layer. The various layers of the patch 12 may be held in tack by suitable adhesive means, heat welding and the like.

Since it is obvious that numerous changes and modifications can be made in the above-described details without departing from the spirit and nature of the invention, it is to be understood that all such changes and modifications are included within the scope of the invention.

I claim:

1. An article for covering a cut area in the skin, comprising a substantially centrally disposed layer of liquid absorbable pad means containing at least a sufficient quantity of a blood coagulating substance consisting essentially of aluminum sulfate, said pad means disposed on a first backing layer having a dimension at least as large as said pad means and being liquid impermeable, said first backing layer being larger than said pad means and including a quantity of a pressure sensitive adhesive thereon, a second backing layer having a dimension larger than said first backing layer and containing a quantity of pressure sensitive adhesive on one surface thereon contacting the non-adhesive surface of said first layer.

2. The article as defined in claim 1 wherein said pad means also includes a member selected from the group consisting of antimicrobial agents, medicaments, antibacterial agents, emolients and suitable mixtures thereof.

3. The article as defined in claim 1 wherein said first backing layer is a flexible plastic member.

4. The article as defined in Claim 1 in roll form sequentially connected and adapted to be sequentially disengaged one from the other.

5. A roll of a plurality of articles as defined in claim 1 disposed in a suitable dispenser.

6. A roll as defined in claim 5 wherein said dispenser includes cutting means.

7. A sheet containing a plurality of articles as defined in claim 1.

* * * * *